United States Patent
Ooms et al.

(10) Patent No.: US 9,175,135 B2
(45) Date of Patent: Nov. 3, 2015

(54) PROCESS FOR PREPARING DIARYL CARBONATES AND POLYCARBONATES

(75) Inventors: Pieter Ooms, Krefeld (DE); Andreas Bulan, Langenfeld (DE)

(73) Assignee: Bayer MaterialScience AG, Leverkusen (DE)

( * ) Notice: Subject to any disclaimer, the term of this patent is extended or adjusted under 35 U.S.C. 154(b) by 158 days.

(21) Appl. No.: 13/071,944

(22) Filed: Mar. 25, 2011

(65) Prior Publication Data

US 2011/0245527 A1    Oct. 6, 2011

(30) Foreign Application Priority Data

Mar. 30, 2010 (EP) ..................... 10158446

(51) Int. Cl.
| | | |
|---|---|---|
| C07C 68/02 | (2006.01) | |
| C08G 64/30 | (2006.01) | |
| C01B 7/04 | (2006.01) | |
| C01B 7/07 | (2006.01) | |

(52) U.S. Cl.
CPC ............... C08G 64/307 (2013.01); C01B 7/04 (2013.01); C01B 7/0731 (2013.01); C07C 68/02 (2013.01)

(58) Field of Classification Search
None
See application file for complete search history.

(56) References Cited

U.S. PATENT DOCUMENTS

| | | | |
|---|---|---|---|
| 2,362,865 A | 11/1944 | Tryon et al. | |
| 2,837,555 A | 6/1958 | Lee | |
| 2,991,273 A | 7/1961 | Hechelhammer et al. | |
| 2,999,835 A | 9/1961 | Goldberg | |
| 2,999,846 A | 9/1961 | Schnell et al. | |
| 3,148,172 A | 9/1964 | Fox | |
| 3,234,263 A | 2/1966 | Kurkjy et al. | |
| 3,271,367 A | 9/1966 | Schnell et al. | |
| 4,012,406 A | 3/1977 | Buysch et al. | |
| 4,764,308 A | 8/1988 | Sauer et al. | |
| 4,982,014 A | 1/1991 | Freitag et al. | |
| 5,104,723 A | 4/1992 | Freitag et al. | |
| 5,126,428 A | 6/1992 | Freitag et al. | |
| 5,136,077 A | 8/1992 | Rand | |
| 5,227,458 A | 7/1993 | Freitag et al. | |
| 5,340,905 A | 8/1994 | Kuhling et al. | |
| 5,424,473 A | 6/1995 | Galvan et al. | |
| 5,473,094 A | 12/1995 | Ooms et al. | |
| 5,478,961 A | 12/1995 | Ooms et al. | |
| 5,527,942 A | 6/1996 | Ooms et al. | |
| 5,602,271 A | 2/1997 | Ooms et al. | |
| 5,679,825 A | 10/1997 | Ooms et al. | |
| 5,710,310 A | 1/1998 | Ooms et al. | |
| 5,831,111 A * | 11/1998 | Ooms et al. ................ 558/274 |
| 5,900,501 A | 5/1999 | Ooms et al. | |
| 6,346,222 B1 | 2/2002 | Abys et al. | |
| 6,387,345 B1 | 5/2002 | Gestermann et al. | |
| 6,402,930 B1 | 6/2002 | Allen et al. | |
| 6,719,957 B2 | 4/2004 | Brady, Jr. et al. | |
| 6,841,047 B2 | 1/2005 | Gestermann et al. | |
| 6,916,953 B2 | 7/2005 | Walsdorff et al. | |
| 7,128,824 B2 | 10/2006 | Bulan et al. | |
| 7,211,177 B2 | 5/2007 | Gestermann | |
| 7,803,259 B2 | 9/2010 | Gestermann et al. | |
| 2003/0024824 A1 | 2/2003 | Bulan et al. | |
| 2003/0166826 A1* | 9/2003 | Miyamoto et al. ............ 528/196 |
| 2003/0173211 A1 | 9/2003 | Gestermann et al. | |
| 2004/0013379 A1 | 1/2004 | Johnson et al. | |
| 2005/0077068 A1 | 4/2005 | Gestermann et al. | |
| 2005/0118088 A1 | 6/2005 | Olbert et al. | |
| 2005/0173257 A1 | 8/2005 | Bulan et al. | |
| 2006/0099138 A1 | 5/2006 | Walsdorff et al. | |
| 2010/0094039 A1 | 4/2010 | Ooms | |

FOREIGN PATENT DOCUMENTS

| | | | |
|---|---|---|---|
| DE | 1570703 A1 | 2/1970 | |
| DE | 1567788 A1 | 5/1970 | |
| DE | 2036052 A1 | 1/1972 | |
| DE | 88 309 A1 | 3/1972 | |
| DE | 2063050 A1 | 7/1972 | |
| DE | 2211956 A1 | 10/1973 | |
| DE | 2447348 A1 | 4/1976 | |
| DE | 3832396 A1 | 2/1990 | |
| DE | 3833953 A1 | 4/1990 | |
| DE | 19535716 A1 | 3/1997 | |
| DE | 101 38 214 A1 | 2/2003 | |
| DE | 10138215 A1 | 2/2003 | |
| DE | 101 48 600 A1 | 4/2003 | |
| DE | 101 52 275 A1 | 4/2003 | |
| DE | 102 00 072 A1 | 7/2003 | |
| DE | 102 03 689 A1 | 8/2003 | |
| DE | 102 34 806 A1 | 2/2004 | |
| DE | 10235476 A1 | 2/2004 | |
| DE | 10250131 A1 | 5/2004 | |
| DE | 103 47 703 A1 | 5/2005 | |
| DE | 102008050828 A1 | 4/2010 | |
| EP | 251731 A1 | 1/1988 | |
| EP | 483632 A2 | 5/1992 | |
| EP | 0516355 A2 | 12/1992 | |
| EP | 635476 A1 | 1/1995 | |
| EP | 635477 A1 | 1/1995 | |
| EP | 645364 A1 | 3/1995 | |

(Continued)

*Primary Examiner* — Michael Barker
*Assistant Examiner* — Po-Chih Chen
(74) *Attorney, Agent, or Firm* — Drinker Biddle & Reath LLP

(57) ABSTRACT

The present invention relates to a process for the continuous preparation of diaryl carbonates from phosgene and at least one monohydroxy compound (monophenol) in the presence of catalysts, and also the use thereof for preparing polycarbonates. The hydrogen chloride formed in the reaction is converted by thermal oxidation into chlorine, with the chlorine being recirculated to the preparation of phosgene. In particular, the process comprises utilization of the hydrogen chloride formed for the process for preparing diphenyl carbonate (DPC process).

18 Claims, 3 Drawing Sheets

(56) References Cited

FOREIGN PATENT DOCUMENTS

| | | |
|---|---|---|
| EP | 691326 A1 | 1/1996 |
| EP | 711599 A1 | 5/1996 |
| EP | 722930 A1 | 7/1996 |
| EP | 757029 A1 | 2/1997 |
| EP | 761593 A1 | 3/1997 |
| EP | 791574 A1 | 8/1997 |
| EP | 808821 A2 | 11/1997 |
| EP | 0931857 A1 | 7/1999 |
| EP | 936184 A2 | 8/1999 |
| EP | 1112997 A2 | 7/2001 |
| FR | 1561518 A | 3/1969 |
| GB | 1046313 A | 10/1966 |
| GB | 1122003 A | 7/1968 |
| GB | 1229482 A | 4/1971 |
| GB | 1341318 A | 12/1973 |
| GB | 1367790 A | 9/1974 |
| JP | 59073405 A | 4/1984 |
| LU | 88569 A1 | 4/1995 |
| RU | 2253607 C1 | 6/2005 |
| SU | 1801943 A1 | 3/1993 |
| WO | WO-91/06526 A1 | 5/1991 |
| WO | WO-97/24320 A1 | 7/1997 |
| WO | WO-00/73538 A1 | 12/2000 |
| WO | WO-02/18675 A2 | 3/2002 |
| WO | WO-03/072237 A1 | 9/2003 |
| WO | WO-2004/014845 A1 | 2/2004 |
| WO | WO-2005/012596 A1 | 2/2005 |

\* cited by examiner

Fig. 1 Integrated process for the preparation of polycarbonate and recycling of the hydrogen chloride formed and the phenol

PROCESS FOR PREPARING DIARYL CARBONATES AND POLYCARBONATES

CROSS-REFERENCE TO RELATED APPLICATIONS

This application claims benefit to European Patent Application No. 10 158 446.4, filed Mar. 30, 2010, which is incorporated herein by reference in its entirety for all useful purposes.

BACKGROUND OF THE INVENTION

The present invention relates to a process for the continuous preparation of diaryl carbonates from phosgene and at least one monohydroxy compound (monophenol) in the presence of catalysts, and also the use thereof for preparing polycarbonates. The hydrogen chloride formed in the reaction is converted by thermal oxidation into chlorine, with the chlorine being recirculated to the preparation of phosgene. In particular, the process comprises utilization of the hydrogen chloride formed for the process for preparing diphenyl carbonates (DPC process).

It is known that diaryl carbonates, in particular diphenyl carbonate, can be prepared by phase boundary phosgenation (Schotten-Baumann reaction) of monophenols in an inert solvent in the presence of alkali and a catalyst. Here, the use of solvents and sodium hydroxide is disadvantageous since the aqueous alkali can cause partial hydrolysis of phosgene or chlorocarbonic esters and large amounts of sodium chloride are obtained as by-product and the solvent and catalyst have to be recovered.

For this reason, the preparation of diaryl carbonates and in particular diphenyl carbonate by reaction of monophenols and phosgene without alkali and without use of solvents in the presence of a catalyst in the direct phosgenation process has also been examined and has been described in principle in the literature.

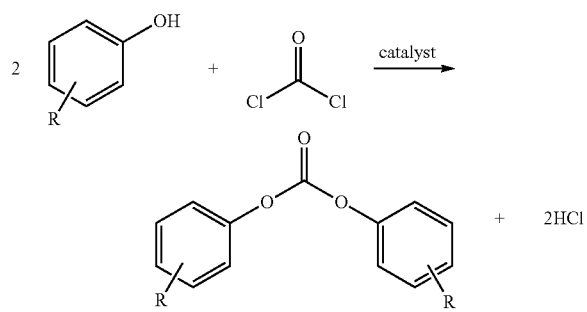

Proposals for processes without solvent using soluble catalysts are described in U.S. Pat. Nos. 2,837,555, 3,234,263 and 2,362,865.

There have also been proposals for using heterogeneous, insoluble catalysts which make the work-up of the reaction mixture substantially easier. Thus, EP 516 355 A2 recommends, in particular, aluminium trifluoride which is applied to supports such as aluminosilicates. However, the synthesis of aluminium fluoride is very complicated and expensive due to the handling of fluorine or hydrofluoric acid.

Furthermore, WO 91/06526 describes metal salts on porous supports as catalysts for the reactions according to the invention. A fully continuous phosgenation of phenol over such catalysts is possible only in the gas phase, but this results in relatively high reaction temperatures and the risk of decomposition of the sensitive chloroformic esters. A phosgenation of phenol using these catalysts in the liquid phase can obviously not be carried out since hot, liquid phenol washes out the active catalyst constituents.

Unsupported catalysts which have the great advantage that the catalyst can be separated off very easily and no impurities remain in the crude reaction product have therefore been proposed. The work-up is substantially simplified thereby.

Thus, processes for preparing diaryl carbonates by phosgenation of monophenols in the presence of heterogeneous catalysts such as activated carbons (EP 483 632), aluminium oxides (EP 635 477), aluminosilicates (EP 635 476), metal oxides (EP 645 364), metalates (EP 691 326), hard materials (EP 722 930) and mixed hydroxides (DE 10 2008 050 828) and also in the presence of homogeneous catalysts such as metal salts (U.S. Pat. No. 634,622), aromatic nitrogen heterocycles (D-A 2 447 348) and organophosphorus compounds (U.S. Pat. No. 5,136,077) both in the liquid phase (EP 757 029, EP 791 574) and also in the gas phase (EP 808 821) have been described.

After synthesis of the diaryl carbonate, the diaryl carbonate is separated off as a mixture with the monophenol used and possibly catalyst or if appropriate in the form of its solution in the organic solvent used in the synthesis, for example chlorobenzene.

To obtain the high-purity diaryl carbonate, a purification by distillation and/or crystallization can be carried out. For example, this is carried out by means of one or more distillation columns connected in series in which any solvent is separated from the diaryl carbonate.

This purification stage or stages can, for example, be carried out continuously in such a way that the temperature at the bottom in the distillation is from 150° C. to 310° C., preferably from 160 to 230° C. The pressure employed for carrying out this distillation is, in particular, from 1 to 1000 mbar, preferably from 5 to 100 mbar.

The diaryl carbonates which have been purified in this way have a particularly high purity (GC>99.95%) and very good transesterification behaviour, so that a polycarbonate can subsequently be prepared in excellent quality therefrom.

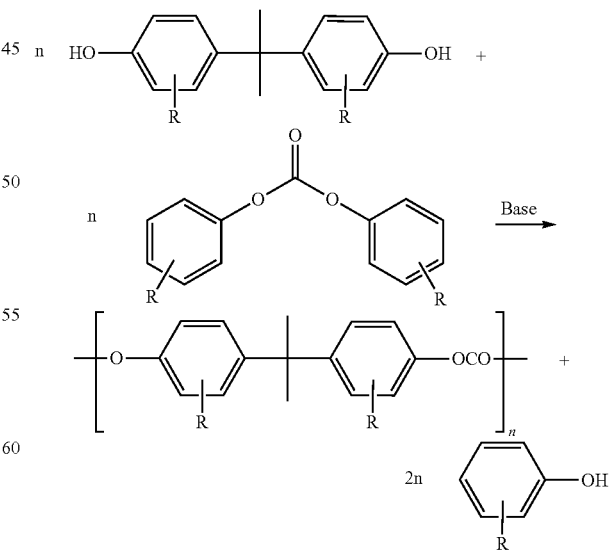

The use of the diaryl carbonates for preparing aromatic oligocarbonates/polycarbonates by the melt transesterification process is known in the literature and is described, for example, in the Encyclopedia of Polymer Science, Vol. 10 (1969), Chemistry and Physics of Polycarbonates, Polymer Reviews, H. Schnell, Vol. 9, John Wiley and Sons, Inc. (1964), pp. 50/51 or U.S. Pat. No. 5,340,905.

The hydrogen chloride formed in the preparation of diphenyl carbonate by direct phosgenation of phenol can be utilized, for example, by marketing of the aqueous solution (hydrochloric acid) or by use in syntheses of other chemical products. However, the amounts of hydrogen chloride obtained cannot always be marketed or used for other syntheses in their entirety. In addition, hydrogen chloride can be used for syntheses only when it is appropriately purified beforehand. On the other hand, marketing is usually only economical when the hydrogen chloride or the hydrochloric acid do not have to be transported over long distances.

One of the most common possible uses of the hydrogen chloride obtained is therefore the use as raw material in PVC production, in which ethylene is oxychlorinated by means of hydrogen chloride to form ethylene dichloride. However, this mode of operation is not generally possible since the corresponding production operations are usually not in the direct vicinity of a diaryl carbonate production plant. Disposal of the hydrogen chloride, e.g. after neutralization with alkali, is unattractive from an economical and ecological point of view.

A recycling process for the hydrogen chloride and recirculation of the chlorine to the diphenyl carbonate production process in which hydrogen chloride is obtained is therefore the desired mode of operation.

A review of electrochemical recycling processes is given in the article "Chlorine Regeneration from Anhydrous Hydrogen Chloride" by Dennie Turin Mah, published in "12$^{th}$ International Forum Electrolysis in Chemical Industry—Clean and Efficient Processing Electrochemical Technology for Synthesis, Separation, Recycle and Environmental Improvement, Oct. 11-15, 1998, Sheraton Sand Key, Clearwater Beach, Fla.".

The recycling of hydrogen chloride by electrochemical oxidation to form chlorine and hydrogen is described in LU 88 569 and EP 1 112 997. A disadvantage is the low current yield and the production of hydrogen which has no use in the polycarbonate production process.

The recycling of hydrogen chloride by thermal reaction with oxygen in the presence of catalysts is also known, as described, for example, in WO 04/014845. A disadvantage here is that the recovery of the phosgenation catalyst pyridine by treatment with alkali leads to a reduced recovery of hydrogen chloride due to the formation of sodium chloride, which has to be disposed of.

Proceeding from the prior art cited above, it was an object of the present invention to provide a diaryl carbonate production process which gives products in high purity and good yield and in which a reduction in environmental pollution or wastewater problems in water treatment plants is achieved by maximized recycling of by-products originating from polycarbonate production. In particular, in the recycling, the conversion of hydrogen chloride into chlorine should be carried out with minimal energy input and therefore in a resource-conserving manner.

It has now been found that hydrogen chloride can be reused particularly advantageously when this hydrogen chloride is converted back into chlorine by thermal oxidation by means of oxygen by the Deacon process and is utilized for preparing phosgene.

The hydrogen chloride obtained in the continuous preparation of diaryl carbonates by reaction of monophenols and phosgene in the presence of catalysts can be passed directly without complicated purification, if appropriate after simple treatment with activated carbon, to a thermal oxidation, with the hydrogen chloride being converted catalytically into chlorine and water and the chlorine being recirculated to the preparation of phosgene.

EMBODIMENTS OF THE INVENTION

An embodiment of the present invention is a process for preparing diaryl carbonate, which comprises the steps of:
  (a) preparing phosgene by reaction of chlorine with carbon monoxide;
  (b) reacting the phosgene formed in step (a) with at least one monophenol in the presence of a catalyst to form at least one diaryl carbonate and hydrogen chloride;
  (c) isolating and working-up the diaryl carbonate formed in step (b);
  (d) isolating and optionally purifying the hydrogen chloride formed in
  (e) thermally oxidizing at least part of the hydrogen chloride from step (d) to chlorine by oxygen with formation of water;
  (f) recirculating at least part of the chlorine prepared in step (e) to the preparation of phosgene in step (a);
  wherein the thermal oxidation by oxygen in step (e) is carried out using one or more catalysts.

Another embodiment of the present invention is the above process, further comprising
  1) cooling the gas mixture formed in step (e) to condense hydrochloric acid;
  2) separating off the resulting aqueous solution of hydrogen chloride (hydrochloric acid) from the gas mixture;
  3) feeding at least part of the hydrochloric acid which has been separated off to an electrochemical oxidation step in which at least part of the aqueous hydrochloric acid is oxidized to chlorine;
  4) optionally adding the chlorine gas obtained from the electrochemical oxidation in step 3) to the gas mixture obtained in step (e);
  5) removing the residual amounts of water present in the gas mixture from steps 3) and (e);
  6) freeing the resulting chlorine-rich gas mixture from oxygen and optionally from secondary constituents.

Another embodiment of the present invention is the above process, wherein the purification of the hydrogen chloride from step (b) takes place before the hydrogen chloride is subjected to thermal oxidation in step (e).

Another embodiment of the present invention is the above process, wherein the hydrogen chloride formed in step (b) is purified in step (d) by removing the phosgene by liquefaction.

Another embodiment of the present invention is the above process, wherein the hydrogen chloride is purified in step (d) by freezing-out.

Another embodiment of the present invention is the above process, wherein the separation of the hydrogen chloride from the gas mixture in steps 2) and 3) comprises scrubbing of the gas mixture with water or dilute hydrochloric acid.

Another embodiment of the present invention is the above process, wherein the electrochemical oxidation of the aqueous hydrogen chloride solution in step 3) is carried out in an electrolysis cell in which the anode space and the cathode space are separated by an ion-exchange membrane.

Another embodiment of the present invention is the above process, wherein the electrochemical oxidation of the aqueous hydrogen chloride solution in step 3) is carried out in an electrochemical cell in which the anode space and the cathode space are separated by a diaphragm.

Another embodiment of the present invention is the above process, wherein the electrochemical oxidation of the aqueous hydrogen chloride solution in step 3) comprises a cathode comprising a gas diffusion electrode.

Another embodiment of the present invention is the above process, wherein the gas diffusion electrode is operated as an oxygen-consuming cathode.

Another embodiment of the present invention is the above process, wherein the cathode comprises rhodium sulphide.

Another embodiment of the present invention is the above process, wherein the hydrochloric acid is oxidized in step 3) together with alkali metal chlorides.

Another embodiment of the present invention is the above process, wherein the hydrochloric acid is oxidized in step 3) together with sodium chloride, in an anodic chloralkali electrolysis.

Another embodiment of the present invention is the above process, wherein a depleted alkali metal chloride solution from the chloralkali electrolysis is used as alkali metal chloride solution.

Another embodiment of the present invention is the above process, wherein part of the hydrogen chloride provided for the thermal oxidation in step (e) is branched off, subjected to absorption in water or dilute hydrochloric acid, and the resulting concentrated solution is combined with the hydrochloric acid from step 2) and fed to the electrolysis in step 3).

Another embodiment of the present invention is the above process, wherein the chlorine is converted into phosgene as per step (a) and the resulting phosgene is used for the reaction with phenol to form diphenyl carbonate in step (b).

Another embodiment of the present invention is the above process, wherein at least one of the diaryl carbonates formed in step b) is diphenyl carbonate.

Another embodiment of the present invention is the above process, wherein the diaryl carbonate is reacted with a bisphenol to form the oligocarbonate/polycarbonate and the monophenol, and wherein the monophenol is used for the reaction with phosgene to form diphenyl carbonate in step (b).

Another embodiment of the present invention is the above process, wherein the thermal oxidation in step (e) is operated at a conversion of from 50 to 98%.

Another embodiment of the present invention is the above process, wherein the removal of the residual amounts of water in step 5) is carried out by scrubbing with sulphuric acid.

DESCRIPTION OF THE INVENTION

Figure 1:
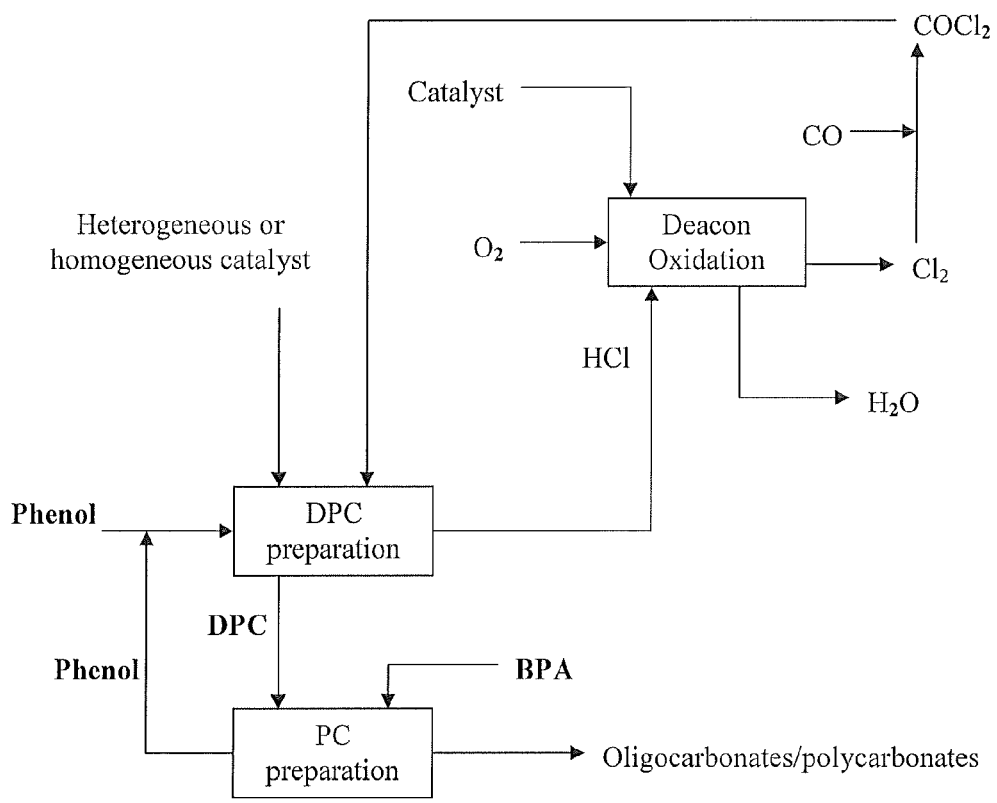
FIG. 1 illustrates a flow diagram of an integrated process for the preparation of polycarbonate and recycling of the hydrogen chloride formed and the phenol.

The present invention accordingly provides a process for preparing diaryl carbonates from monophenols and carbonyl dihalide, which is characterized in that the hydrogen halide formed is converted by thermal oxidation by means of an oxygen-containing gas by the Deacon process into the halogen and this is in turn converted, after isolation and by reaction with carbon monoxide, into the carbonyl dihalide which can subsequently be used for reaction with the monophenol to produce the diaryl carbonate. The monophenol which is liberated in the preparation of solvent-free polycarbonate by transesterification of diaryl carbonates and bisphenols can be reused for preparing the diaryl carbonate. The present patent application further provides a process in which the diaryl carbonate prepared is used for preparing polycarbonate.

The overall process of the invention is flexible, simple to carry out and gives products in high purity, which is extraordinarily important for the overall process, with simultaneous reduction of environmental pollution by reuse, comprising the following process steps (cf. FIG. 1):

(a) preparation of phosgene by reaction of chlorine with carbon monoxide, (b) reaction of the phosgene formed in step (a) with at least one monophenol in the presence of a catalyst and optionally an organic solvent to form at least one diaryl carbonate and hydrogen chloride, (c) isolation and work-up of the diaryl carbonate formed in step (b), (d) isolation and optionally purification of the hydrogen chloride formed in step (b), (e) thermal oxidation of at least part of the hydrogen chloride from (d) to chlorine by means of oxygen with formation of water, where the thermal oxidation is carried out using one or more catalysts, (f) recirculation of at least part of the chlorine prepared in step (e) to the preparation of phosgene in step (a).

The gas mixture consisting of the target products chlorine and water, unreacted hydrogen chloride and oxygen and also further secondary constituents, in particular carbon dioxide and nitrogen, which is formed in the reaction (e) is optionally 1) cooled to condense hydrochloric acid, 2) the resulting aqueous solution of hydrogen chloride (hydrochloric acid) is separated off from the gas mixture, 3) the hydrochloric acid which has been separated off is at least partly fed to an electrochemical oxidation in which at least part of the aqueous hydrochloric acid is oxidized to chlorine, 4) the chlorine gas obtained in step 3) is optionally added to the gas mixture obtained in step (e), 5) the residual amounts of water present in the gas mixture from steps 3) and (e) are removed, in particular by scrubbing with sulphuric acid, 6) the resulting chlorine-rich gas mixture is freed of oxygen and optionally of secondary constituents.

The thermal oxidation by means of oxygen by the Deacon process leads to improved economics compared to a classical electrolysis which in addition to chlorine produces hydrogen which has no use in the preparation of diaryl carbonate or polycarbonate.

In a particularly preferred embodiment, at least part of the diaryl carbonate prepared in step (c) is reacted with a bisphenol to form oligocarbonate/polycarbonate and the monophenol (the transesterification reaction). The monophenol formed in the transesterification can, in a further preferred embodiment, again be used in step (b).

The process of the invention is a process for the preparation of diaryl carbonates and the thermal oxidation of the hydrogen chloride by means of oxygen to recover chlorine for the synthesis of phosgene as starting material for the preparation of diaryl carbonate.

In the first step (a) of the process of the invention, phosgene is prepared by reaction of chlorine with carbon monoxide. The synthesis of phosgene is adequately known and is described, for example, in Ullmanns Enzyklopädie der industriellen Chemie, 3rd edition, volume 13, pages 494-500. On an industrial scale, phosgene is prepared predominantly by reaction of carbon monoxide with chlorine preferably over activated carbon as catalyst. The strong exothermic gas-phase reaction occurs at temperatures of from at least 250° C. to a maximum of 600° C., generally in shell-and-tube reactors. The heat of reaction can be removed in various ways, for example by means of a liquid heat transfer medium as described, for example, in WO 03/072237 or by evaporative cooling in a secondary cooling circuit with simultaneous utilization of the heat of reaction for generation of steam, as disclosed, for example, in U.S. Pat. No. 4,764,308.

Phosgene formed in step (a) is reacted with at least one monophenol in a next process step (b) to form at least one diaryl carbonate. The process step (b) will hereinafter also be referred to as phosgenation. The reaction forms hydrogen chloride as by-product.

The synthesis of diaryl carbonates is likewise adequately known from the prior art, with the monophenol generally being used in a stoichiometric excess over phosgene. The phosgenation (b) usually takes place in the liquid phase, with the phosgene and the monophenol being able to be dissolved in the melt, optionally in a solvent. Preferred solvents are chlorinated aromatic hydrocarbons such as chlorobenzene, o-dichlorobenzene, p-dichlorobenzene, trichlorobenzenes, the corresponding chlorotoluenes or chloroxylenes, toluene, xylenes and the monophenol itself.

Particular preference is given to using the molten monophenol as solvent.

In another, preferred embodiment, the phosgenation takes place in the gas phase. The gas-phase phosgenation is described, for example, in U.S. Pat. No. 5,831,111.

Monophenols suitable for the process of the invention are phenols of the formula (I)

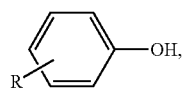

(I)

where
R is hydrogen, halogen or a branched or unbranched $C_1$-$C_9$-alkyl radical, $C_1$-$C_9$-alkoxy radical or $C_1$-$C_9$-alkoxycarbonyl radical.

Preference is thus given to phenol, alkylphenols such as cresols, p-tert-butylphenol, p-cumylphenol, p-n-octylphenol, p-isooctylphenol, p-n-nonylphenol and p-isononylphenol, halogenated phenols such as p-chlorophenol, 2,4-dichlorophenol, p-bromophenol, 2,4,6-tribromophenol, anisole and methyl or phenyl salicylate. Particular preference is given to phenol.

Both heterogeneous and homogeneous catalysts can be used for the process of the invention.

As heterogeneous catalysts, it is possible to use activated carbons (EP 483 632), aluminium oxides (EP 635 477), aluminosilicates (EP 635 476), metal oxides (EP 645 364), metalates (EP 691 326), hard materials (EP 722 930) and mixed hydroxides (DE 10 2008 050 828) both in the liquid phase (EP 757 029, EP 791 574) and in the gas phase (EP 808 821).

As homogeneous catalysts, it is possible to use metal salts, alkoxides thereof or organophosphorus compounds.

It is possible to use one or more, activated or unactivated catalysts.

Suitable catalysts for step b) of the process of the invention are:
a) activated carbons which have surface areas determined by the BET method of from 200 to 3000 m2/g and have been produced from sawdust and other wood wastes, straw, types of coal, nut shells, mineral oil tars, lignin, polysaccharides, polyacrylonitrile, bones, peat or coke products from brown or hard coals, preferably from wood, cellulose, lignin, bituminous or brown coal, peat or hard coal coke,
b) aluminosilicates selected from the group of zeolites of the general formula $$M_{2/n}O.xSiO_2.Al_2O_3.yH_2O$$

where
M is a cation such as a proton or a metal cation of the Mendeleev Periodic Table of the Elements,
n is the valency of the cation,
x is the molar ratio of $SiO_2:Al_2O_3$, where
x can be 1.0-50.0, and
y is 0-9,
or zeolite-like compounds such as ALPOs and SAPOs or sheet silicates of the kaolin, serpentine, montmorillonite and bentonite types or "pillared clays" or $SiO_2/Al_2O_3$ precipitated catalysts,
c) aluminium oxides or y-aluminium oxides having surface areas determined by the BET method of from 2 to 500 m²/g,
d) oxide(s) of metals of group IVB of the Periodic Table, for example oxides of titanium, zirconium or hafnium, having surface areas determined by the BET method of from 2 to 500 m²/g,
e) metalates of the general formula $$A_xB_yO_z$$

where
A is a monovalent, divalent or trivalent metal cation and
B is a trivalent, tetravalent, pentavalent and/or hexavalent metal cation and
x is from 1 to 4 and
y is 1 or 2 and
z is 3, 6, 7 or 9,
f) hard materials having metal-like properties (ceramic precursors) of the general formula $$A_xB_yC_zD_w$$

where
A is an element of groups 3 to 10, 13 and 14 of the Periodic Table of the Elements (IUPAC Notation) and
B is an element of groups 13, 14, 15 and 16 with the exception of oxygen,
C is an element of groups 14 and 15 and
D is an element of groups 14 and 15 and
x is from 1 to 4 and
y is from 1 to 4 and
z is from 0 to 4 and
w is from 0 to 4,
where A, B, C and D each come from different groups or in the case of the same group from different periods, with the proviso that A is not aluminium when B is carbon and z and w are simultaneously 0,
g) mixed hydroxides of the general formula (III)

$$[M(II)_{1-x}M(III)_xM(IV)_y(OH)_2]A^{n-}{}_{z/n}.mH_2O \qquad (III),$$

where
M (II) is a divalent metal cation and
M (III) is a trivalent metal cation and
M (IV) is a tetravalent metal cation and x is from 0.1 to 0.5 and
y is from 0 to 0.5,
z is 1+y and
m is from 0 to 1,
A is an inorganic anion such as $OH^-$, $NO_3^-$, $CO_3^{2-}$, $SO_4^{2-}$, $CrO_4^{2-}$ or $Cl^-$,
n is from 1 to 2,
h) metal salts, halides, alkoxides and phenoxides such as $AlCl_3$, $AlF_3$, $ZrCl_4$, $TiCl_4$, $VCl_3$, $VCl_4$ or $Ti(OC_6H_5)_4$,
i) organophosphorus compounds, homogeneous or optionally bound to a polymer.

The homogeneous catalysts can optionally be applied to an inert support, as described in JP 695219, WO 91/06526, U.S. Pat. No. 5,424,473 and EP 516 355.

Preference is given to aluminium oxide, titanium oxide, zirconium oxide, calcium titanate, magnesium titanate and magnesium aluminium hydrotalcite, which are preferably used as fixed bed in the novel process, and titanium chloride, zirconium chloride, aluminium chloride and titanium phenoxide, which are used as homogeneous catalysts.

Particular preference is given to aluminium oxide and $TiCl_4$.

The catalyst is used in amounts of from 0.5 to 100% by weight based on the amount of monohydroxy compound (monophenol) in a not fully continuous mode of operation or at space velocities of from 0.1 to 20 g of monohydroxy compound (monophenol) per g of catalyst per hour in the case of a fully continuous mode of operation.

Phosgene can be used in liquid or gaseous form or optionally as a solution in an inert solvent in process step (b).

Inert organic solvents which may optionally be used in step (b) of the novel process are, for example, toluene, chlorobenzene, dichlorobenzene and chlorotoluene, with preference being given to phenol itself.

If phosgenation in the gas phase is selected, the reaction is carried out above the boiling point of phenol, preferably at an average contact time of from 0.5 to 5 seconds and at temperatures of from 180 to 500° C.

In the phosgenation in the liquid phase, temperatures of from 20 to 240° C. and pressures of from 1 to about 50 bar are usually set. The phosgenation in the liquid phase can be carried out in one or more stages, with phenol generally being able to be used in a stoichiometric excess.

The phenol and the phosgene can be combined by means of a static mixing element, passed in countercurrent or cocurrent over, for example, a fixed bed (heterogeneous) or through one or more reactive distillation columns or bubble columns (homogeneous) where the mixture reacts to form the desired diaryl carbonate and hydrogen chloride. Apart from reaction towers provided with suitable mixing elements, reaction vessels having a stirrer can also be used. Apart from static mixing elements, it is also possible to use specific dynamic mixing elements. Suitable static and dynamic mixing elements are known from the prior art.

After the phosgenation in step (b), the diaryl carbonates formed in the phosgenation are, according to the invention, separated off in step (c). This is achieved by firstly separating the reaction mixture from the phosgenation into a liquid product stream and a gaseous product stream in a manner known to those skilled in the art. The liquid product stream contains essentially the diaryl carbonate, if appropriate the solvent and a small proportion of unreacted phosgene. The gaseous product stream consists essentially of hydrogen chloride gas, unreacted phosgene and also small amounts of any solvent and inert gases, for example nitrogen and carbon monoxide. The liquid stream in step (c) is subsequently passed to a work-up, preferably a work-up by distillation in which phosgene and if appropriate the solvent are separated off in succession. In addition, a further work-up of the diaryl carbonates formed is optionally carried out in step (c). This is achieved, for example, by the diaryl carbonate obtained being purified in a manner known to those skilled in the art by distillation or crystallization.

The purification of the hydrogen chloride which may be necessary in step (d) can be required because the hydrogen chloride obtained in the reaction of phosgene with a phenol generally contains organic constituents which can interfere in the thermal oxidation of hydrogen chloride in step (e), so that the catalyst has to be replaced when the catalytically active material is deactivated by contamination or damage. Such organic constituents include, for example, phosgene, the monophenol or any solvent used in the preparation of diaryl carbonate, e.g. chlorobenzene, o-dichlorobenzene or p-dichlorobenzene. If the thermal oxidation is carried out by the Deacon process in the gas phase in the presence of catalysts, the function of the catalyst could be impaired by these organic constituents. The impurities can also deposit on the catalyst and in this way reduce the activity, which results in a reduction of the chlorine yield.

Accordingly, the hydrogen chloride produced in the phosgenation in step (b) is separated from the gaseous product stream in a further process step (d). The gaseous product stream which is obtained in the isolation of the diphenyl carbonate in step (c) is treated in step (d) to separate off the phosgene, with the hydrogen chloride being able, optionally after purification, to be fed to a thermal oxidation as per step (e).

The isolation of the hydrogen chloride in step (d) is effected by firstly separating off phosgene from the gaseous product stream. The phosgene is separated off by liquefaction of phosgene, for example at one or more condensers connected in series. The liquefaction is preferably carried out at temperatures in the range from −15 to −40°. In addition, any amount of organic impurities such as monophenol can be removed from the gaseous product stream by this cooling to low temperatures.

In addition or as an alternative, the phosgene can be washed out of the gas stream in one or more stages by means of cold solvent or solvent/phosgene mixture. Suitable solvents for this purpose are, for example, the chlorobenzene and o-dichlorobenzene which may have already been used in the phosgenation. The temperature of the solvent or solvent/phosgene mixture is for this purpose in the range from −15 to −46° C.

The phosgene which has been isolated from the gaseous product stream can be fed back to the phosgenation in step (b).

The hydrogen chloride may subsequently be purified in step (d) to reduce the proportion of organic impurities such as unreacted monophenol. This can be effected by means of, for example, freezing-out, in which, depending on the physical properties of the monophenol, the hydrogen chloride is, for example, passed through one or more cold traps.

In a preferred embodiment of the purification of the hydrogen chloride which may be provided in step (d), the hydrogen chloride stream is passed through two heat exchangers connected in series, with the monophenol to be separated off being frozen out at, for example, −40° C., depending on the freezing point. The heat exchangers are operated alternately, with the gas stream thawing the monophenol previously frozen out in the heat exchanger through which the stream has been passed first. The monophenol can be reused for the preparation of the diaryl carbonate. In the downstream second heat exchanger which is supplied with a conventional heat transfer medium for refrigeration machines, e.g. a compound from the group of Frigens, the gas is cooled to below the freezing point of the monophenol so that the latter crystallizes out. After the thawing and crystallization operations are concluded, the gas stream and the cooling stream are switched over, so that the function of the heat exchangers is reversed. The gas stream containing hydrogen chloride can in this way be depleted to a monophenol content of preferably not more than 500 ppm, particularly preferably not more than 50 ppm, very particularly preferably not more than 20 ppm.

As an alternative, the purification of the hydrogen chloride can be carried out in two heat exchangers connected in series, as described in U.S. Pat. No. 6,719,957. Here, the hydrogen chloride is compressed to a pressure of from 5 to 20 bar, preferably from 10 to 15 bar, and the compressed gaseous hydrogen chloride is fed at a temperature of from 20 to 60° C., preferably from 30 to 50° C., to a first heat exchanger. In this, the hydrogen chloride is cooled to a temperature of from −10 to −30° C. by a cold hydrogen chloride coming from a second heat exchanger. This results in condensation of organic constituents which can be passed to disposal or reuse. The hydrogen chloride introduced into the first heat exchanger leaves the latter at a temperature of from −20 to 0° C. and is cooled in the second heat exchanger to a temperature of from −10 to −30° C. The condensate formed in the second heat exchanger consists of further organic constituents and also small amounts of hydrogen chloride. To avoid a loss of hydrogen chloride, the condensate flowing out of the second heat exchanger is fed to a separation and vaporization unit. This can be, for example, a distillation column in which the hydrogen chloride is driven off from the condensate and recirculated to the second heat exchanger. It is also possible to recirculate the hydrogen chloride which has been driven off to the first heat exchanger. The hydrogen chloride which has been cooled in the second heat exchanger and freed from organic constituents is introduced at a temperature of from −10 to −30° C. into the first heat exchanger.

After heating to from 10 to 30° C., the hydrogen chloride which has been freed from organic constituents leaves the first heat exchanger.

In an alternative process, the purification of the hydrogen chloride which is optionally provided in step (d) is carried out by means of adsorption of organic impurities such as residues of monophenol on activated carbon. Here, for example, the hydrogen chloride is, after removal of excess phosgene, passed over or through a bed of activated carbon at a pressure of from 0 to 5 bar, preferably from 0.2 to 2 bar. The flow rates and residence times are matched to the content of impurities in a manner known to those skilled in the art. The adsorption of organic impurities can likewise be carried out on other suitable adsorbents, e.g. zeolites.

In a further alternative process, a distillation of the hydrogen chloride can be provided for the purification of the hydrogen chloride which may optionally be provided in step (d). This is effected after condensation of the gaseous hydrogen chloride. In the distillation of the condensed hydrogen chloride, the purified hydrogen chloride is taken off as overhead product from the distillation, with the distillation being carried out under conditions of pressure, temperature and the like which are customary for such a distillation and are known to those skilled in the art.

After purification, the hydrogen chloride is reacted with oxygen, optionally in the presence of a catalyst.

The reaction can be carried out in the presence of catalysts at a temperature of from about 250 to 450° C. The usual reaction pressure is in the range from 1 to 10 bar. Various embodiments of the process, which is generally known as the Deacon process, have been described: the Shell chlorine process, the MT chlorine process, the KEL chlorine process, the Carrier Catalyst process and the Sumitomo chlorine process.

Suitable catalysts for the Deacon process contain transition metal compounds such as copper compounds and ruthenium compounds or else compounds of other noble metals such as gold and palladium. Such catalysts are described, for example, in the documents DE 1 567 788 A1, EP 251 731 A2, EP 936 184 A2, EP 761 593 A1, EP 711 599 A1 and DE 102 50 131 A1. The catalysts are generally applied to a support. These supports comprise, for example, silicon dioxide, aluminium oxide, titanium dioxide or zirconium oxide.

The Deacon processes are generally carried out in fluidized-bed reactors or fixed-bed reactors, e.g. in shell-and-tube reactors. Hydrogen chloride is freed from impurities before the reaction in order to avoid poisoning of the catalysts used. The reaction can be carried out essentially isothermally or essentially adiabatically.

As an alternative thereto, processes in which the reaction of hydrogen chloride with oxygen is activated nonthermally are known. Such processes are described in "W. Stiller, Nichtthermische aktivierte Chemie, Birkhäuser Verlag, Basle, Boston, 1987, pp. 33-34, pp. 45-49, pp. 122-124, pp. 138-145". Specific embodiments are disclosed, for example, in the documents RU 2253607, JP-A-59073405, DD-A-88 309, SU 1801943 A1. For the present purposes, nonthermally activated reactions are, for example, reactions induced by the following means or processes:

high-energy radiation, e.g. laser radiation, photochemical radiation sources, UV radiation, infrared radiation, etc.,
a low-temperature plasma, e.g. generated by means of an electric discharge,
magnetic field activation,
tribomechanical activation, e.g. activation by means of shock waves,
ionizing radiation, e.g. gamma-rays and X-rays, α-radiation and β-radiation from nuclear disintegrations, high-energy electrons, protons, neutrons and heavy ions,
microwave irradiation.

The oxygen-containing gas is, both in the case of thermally activated and nonthermally activated reaction of hydrogen chloride with oxygen, generally used as pure gas having an $O_2$ content of >98% by volume. However, smaller proportions of oxygen are also possible. Apart from oxygen, the oxygen-containing gas can also contain, for example, nitrogen or carbon dioxide.

It is common to all known processes that the reaction of hydrogen chloride with oxygen gives a gas mixture which contains not only the target product chlorine but also water, unreacted hydrogen chloride and oxygen and also further secondary constituents such as carbon dioxide. To isolate pure chlorine, the product gas mixture is cooled after the reaction to such an extent that water of reaction and hydrogen chloride condense out in the form of concentrated hydrochloric acid. The hydrochloric acid formed is separated off and the remaining gaseous reaction mixture is freed from residual water by scrubbing with sulphuric acid or other methods such as drying by means of zeolites.

The hydrochloric acid which has been separated off is preferably fed to a desorption stage in which the gaseous hydrogen chloride is liberated again. This gaseous hydrogen chloride can be recirculated either partly or preferably completely to the reaction of hydrogen chloride with oxygen. The dilute hydrochloric acid obtained in the desorption stage can be recirculated to the hydrochloric acid condensation stage. Here, the dilute hydrochloric acid serves as absorption medium for the gaseous hydrogen chloride to be separated off. Such a procedure is described, for example, in the document DE 102 35 476 A1. As an alternative, the hydrochloric acid which has been separated off can also be passed to another use.

The chlorine-containing reaction gas mixture which has been freed from residual water is, in a preferred embodiment, subsequently compressed, with oxygen and other gas constituents remaining in the gas phase and being able to be separated off from the liquefied chlorine. Such processes for isolating pure chlorine from gas mixtures are described, for example, in the documents DE 195 35 716 A1 and DE 102 35 476 A1. The now purified chlorine can then be passed to the use, for example the preparation of phosgene.

In the next process step (f), at least part of the chlorine prepared in step (e) is, according to the invention, recirculated with the preparation of phosgene in step (a). Before recirculation, the chlorine is preferably cooled and dried in a single-stage or multistage cooling operation by means of a cooling apparatus, e.g. a shell-and-tube heat exchanger. Drying can be carried out, for example, by means of a suitable desiccant in an absorption column provided with mass transfer elements. A suitable desiccant can be, as described, for example, in DE 10 235 476 A, either molecular sieves or hygroscopic adsorbents, e.g. sulphuric acid. Drying can be carried out in one or more stages. Drying is preferably carried out in two stages, with the chlorine to be dried being brought into contact with a sulphuric acid having a relatively low concentration, preferably from 70 to 80%, particularly preferably from 75 to 80%, in a first stage. In a second stage, the residual moisture is removed from the chlorine by means of a sulphuric acid having a higher concentration of preferably from 88 to 96%, particularly preferably 92-96%. The chlorine which has been dried in this way and has a residual moisture content of preferably not more than 100 ppm, particularly preferably not more than 20 ppm, can be passed through a droplet precipitator to remove any sulphuric acid droplets still present therein.

After preparation of an aqueous hydrogen chloride solution as per steps 1) and 2) and, if appropriate, after purification of the aqueous hydrogen chloride solution, the hydrochloric acid is fed to an electrolysis cell. The electrochemical oxidation of the hydrochloric acid as per step 3) is carried out by the membrane process.

According to WO 97/24320, it is possible to use, inter alia, solid electrolyte systems, e.g. Nafion® membranes, with the cathode being arranged on one side of the ion-exchange membrane. The cathode is, for example, a gas diffusion electrode. The catalytically active material of the cathode is incorporated into the ion-exchange membrane or can be applied to the ion-exchange membrane.

The electrochemical oxidation of an aqueous solution of hydrogen chloride using a gas diffusion electrode as cathode is described, for example, in WO 00/73538 and WO 02/18675. Here, rhodium sulphide is used as catalyst for the reduction of oxygen at the cathode. According to WO 02/18675, this catalyst is largely resistant to organic constituents which can be present as impurities in the hydrochloric acid and originate, for example, from preceding steps of the synthesis. The organic constituents go from the anode space through the ion-exchange membrane into the cathode space.

The electrochemical oxidation of hydrochloric acid in step (3) can be carried out by the membrane process in a two-chamber electrolysis cell consisting of anode space and cathode space or in a three-chamber electrolysis cell consisting of anode space, cathode space and an electrolyte space between anode space and cathode space. A two-chamber electrolysis cell is preferably selected. In the membrane process, the anode space is separated from the cathode space by an ion-exchange membrane (hereinafter also referred to as membrane in the interests of simplicity), in particular a cation-exchange membrane. The distance of the electrodes (anode and cathode) from the membrane is preferably from 0 to 3 mm, particularly preferably from 0 to 2 mm. Suitable ion-exchange membranes are commercially available, e.g. single-layer ion-exchange membranes having sulphonic acid groups. For example, it is possible to use a membrane of the Nafion® 117 type from DuPont.

The electrolysis of hydrochloric acid by the membrane process can be carried out using electrodes containing graphite, with the anode being able to consist of graphite.

In a preferred embodiment, the electrochemical oxidation of the aqueous solution of hydrogen chloride in step (3) is carried out by a membrane process using a gas diffusion electrode as oxygen-depolarized cathode. Here, the electrolysis cell can consist of either two chambers or three chambers, but preferably of two chambers. An oxygen-containing gas, e.g. oxygen, air or oxygen-enriched air, is fed to the cathode half cell. The oxygen is reduced at the gas diffusion electrode to form water. The anode half cell is supplied with the aqueous hydrogen chloride solution, with the hydrogen chloride being oxidized to chlorine at the anode. The anode half cell and the cathode half cell are separated from one another by a cation-exchange membrane. The electrolysis of hydrochloric acid using a gas diffusion electrode as cathode is described, for example, in WO 00/73538.

The electrolysis cell can comprise either a nonmetallic material as described in DE 103 47 703 A or a metallic material. Suitable metallic materials for the electrolysis cell are, for example, titanium and titanium alloys, e.g. a titanium-palladium alloy. Here, the half shells for the anode and cathode half cells, the current distributor and the power leads are made of titanium or a titanium alloy.

The anode can, for example, be configured as described in DE 102 34 806 A. Here, the anode comprises metal, preferably titanium with a coating of noble metal oxide, e.g. ruthenium oxide. Furthermore, the titanium anode as described in DE 102 00 072 A can have an intermediate layer of titanium carbide or titanium boride which is applied to the titanium anode by means of plasma or flame spraying before the coating of a noble metal oxide is applied. According to DE 102 34 806 A, the metal anode has openings for passage of the gas formed during the electrolysis, with the openings preferably having guide structures which discharge the gas formed to the side of the metal anode facing away from the ion-exchange membrane. Here, the total cross-sectional area of the openings should be in the range from 20% to 70% of the area formed by the height and width of the anode. The metal anode can also have a wave-like, zig-zag or rectangular cross section. The depth of the anode should be at least 1 mm. The ratio of electrochemically active area of the metal anode to the area formed by the height and width of the metal electrode should be at least 1.2. In a specific embodiment, the metal anode can comprise two adjacent expanded metals, with the expanded metal facing the ion-exchange membrane being more finely structured than the expanded metal facing away from the ion-exchange membrane. Furthermore, the more finely structured expanded metal is rolled flat and the more coarsely structured expanded metal is arranged so that the struts are inclined in the direction of the cathode and serve as guide structures. As an alternative, the anode can also consist of an expanded metal. The anode should basically have a free area of from 15 to 70%. The thickness of the expanded metals should be selected so that there is no additional electrical resistance to an electrolyzer in the case of bipolar connection of the individual electrolysis cells (cell elements). The electrical resistance depends essentially on the electrical contacting of the anode, for example the number of current-supplying connecting elements between anode and back wall of the anode half cell.

In the electrolysis by means of a gas diffusion electrode, the anode space and the cathode space can be separated by a commercial ion-exchange membrane. For example, it is possible to use ion-exchange membranes of the Nafion® 324 or Nafion® 117 types from DuPont. Preference is given to using a membrane which, as described in WO 05/12596, has a smooth surface structure on the side facing the gas diffusion electrode. The smooth surface structure of the membrane allows the gas diffusion electrode and the membrane to be juxtaposed in such a way that under a pressure of 250 g/cm$^2$ and a temperature of 60° C. the contact area is at least 50% of the geometric area of the membrane.

The cathodic current distributor to which the gas diffusion electrode is applied is preferably configured as described in DE 102 03 689 A. This has a free area of less than 65% but more than 5%. The thickness of the current distributor is at least 0.3 mm. It can comprise an expanded metal, mesh, woven fabric, foam, nonwoven, slotted sheet or perforated plate made of metal. The cathodic current distributor preferably comprises an expanded metal having a mesh length of from 4 to 8 mm, a mesh width of from 3 to 5 mm, a strut width of from 0.4 to 1.8 mm and a thickness of from 0.4 to 2 mm. In addition, the cathodic current distributor can have a second expanded metal as support for the first expanded metal. The second expanded metal as support preferably has a mesh length of from 10 to 40 mm, a mesh width of from 5 to 15 mm, a strut width of from 2 to 5 mm and a thickness of from 0.8 to 4 mm. It is also possible to use a mesh which preferably has a wire thickness of from 1 to 4 mm and a mesh opening of from 7 to 25 mm as support. Furthermore, a perforated metal sheet or slotted metal sheet which preferably has an open area of less than 60% and a thickness of from 1 to 4 mm can be used as support. As material for the cathodic current distributor, it is possible to use, for example, titanium or a noble metal-containing titanium alloy, e.g. titanium-palladium. If the current distributor is an expanded metal, this is preferably rolled.

As gas diffusion electrode, it is possible to use a commercial gas diffusion electrode which is equipped with a suitable catalyst. Suitable catalysts contain, according to WO 00/73538, rhodium and/or at least one rhodium sulphide or a mixture of rhodium and at least one rhodium sulphide. According to EP 931 857 A, it is also possible to use rhodium and/or rhodium oxide or mixtures thereof. The gas diffusion electrode preferably comprises an electrically conductive woven fabric, paper or nonwoven composed of carbon, with the woven fabric, paper or nonwoven being provided on one side with a carbon-containing catalyst layer and on the other side with a gas diffusion layer. The catalyst is preferably applied to a support, preferably a carbon support, with polytetrafluoroethylene particles which are coupled to the support structure being integrated. The gas diffusion layer preferably comprises carbon and polytetrafluoroethylene particles in a ratio of carbon to PTFE of, for example, 50:50. The gas diffusion electrode can, for example, be arranged so that it is not firmly joined to the ion-exchange membrane. Contact between the gas diffusion electrode and the current distributor and the ion-exchange membrane is preferably established by pressed contact, i.e. the gas diffusion electrode, the current distributor and the membrane are pressed together. The gas diffusion electrode can be connected to the current collector as described in DE 101 48 600 A.

The electrolysis of hydrochloric acid by the membrane process using a gas diffusion electrode is usually carried out at a temperature of from 40 to 70° C. The concentration of the aqueous solution of hydrogen chloride in the anode space is from 10 to 20% by weight, preferably from 12 to 17% by weight. The cell can, for example, be operated with the pressure in the anode space being higher than the pressure in the cathode space. This results in the cation-exchange membrane being pressed onto the gas diffusion electrode and in this in turn being pressed onto the current distributor. As an alternative, a construction of the electrolysis cell as described in DE 101 38 214 A can be selected. The anode and/or the current distributor are mounted elastically, for example by being joined by means of springs to the back wall of the respective half cell. Assembly of this cell forms a zero gap arrangement in which the anode is in direct contact with the ion-exchange membrane and the latter is in turn in direct contact with the gas diffusion electrode and this gas diffusion electrode is in turn in direct contact with the current distributor. The elastic mounting presses together the anode, membrane, gas diffusion electrode and current distributor.

In a preferred embodiment of the electrolysis process, the anode half element is filled with a 5 to 20% strength by weight hydrochloric acid when starting up the electrolysis cell as described in DE 10 152 275 A, where the hydrochloric acid contains at least 10 ppm of free chlorine and the concentration of the hydrochloric acid during start-up is more than 5% by weight. The volume flow of hydrochloric acid through the anode space is set so that at the beginning of the electrolysis the hydrochloric acid flows at a velocity of from 0.05 to 0.15 cm/s through the anode space. The electrolysis is started at a current density of from 0.5 to 2 kA/m$^2$ and is increased at time intervals of from 5 to 25 minutes by in each case from 0.5 to 1.5 kA/m$^2$. After a prescribed current density of preferably from 4 to 7 kA/m$^2$ has been reached, the volume flow of the hydrochloric acid is set so that the hydrochloric acid flows at a velocity of from 0.2 to 0.4 cm/s through the anode half element.

A particularly advantageous mode of operation of the electrolysis cell can be effected as described in DE 101 38 215 A, according to which the electrolysis cell is operated with an elevated pressure in the cathode chamber to lower the cell potential. The differential pressure between anode space and cathode space should be from 0.01 to 1000 mbar and the oxygen pressure in the cathode space should be at least 1.05 bar absolute.

The circulatory mode of operation of the process of the invention requires a further partial amount of chlorine to be provided in addition to the chlorine prepared by means of thermal oxidation in step (e) for the preparation of phosgene in step (a) since losses of chlorine and hydrogen chloride occur in the chlorine-hydrogen chloride circuit. The provision of a further partial amount of chlorine can be effected in the form of elemental chlorine from an external source, for example the electrolysis of an aqueous sodium chloride or hydrochloric acid solution. However, the losses of chlorine and hydrogen chloride which occur can also be compensated by providing a partial amount of hydrogen chloride from an external source, e.g. from an isocyanate production plant (e.g. MDI, TDI) in which hydrogen chloride is obtained as gaseous by-product. A partial amount of hydrogen chloride in the form of an aqueous hydrogen chloride solution from an external source, e.g. from a production process in which an aqueous hydrogen chloride solution is obtained as by-product, is preferably fed at about 30% strength by weight hydrochloric acid to an electrolysis. A hydrochloric acid having a lower concentration can alternatively be fed to the absorption of hydrogen chloride.

The phosgene can be reused in the preparation of the diaryl carbonate in step (b).

Transesterification of the diaryl carbonate prepared in step (b) with at least one bisphenol gives an oligocarbonate/polycarbonate and monophenol which can in turn be used in step (b).

Bisphenols suitable for the process of the invention are dihydroxydiarylalkanes of the formula (II),

$$HO-Z-OH \qquad (II)$$

where Z is a divalent organic radical which has from 6 to 30 carbon atoms and contains one or more aromatic groups. Examples of such compounds which can be used in step (a) of the process of the invention are dihydroxydiarylalkanes such as hydroquinone, resorcinol, dihydroxybiphenyl, bis(hydroxyphenyl)alkanes, bis(hydroxylphenyl)cycloalkanes, bis(hydroxyphenyl)sulphides, bis(hydroxyphenyl)ethers, bis(hydroxyphenyl)ketones, bis(hydroxyphenyl)sulphones, bis(hydroxylphenyl)sulphoxides, α,α'-bis(hydroxyphenyl)diisopropylbenzenes, and also alkylated, ring-alkylated and ring-halogenated derivatives thereof.

Preferred bisphenols are 4,4'-dihydroxybiphenyl, 2,2-bis(4-hydroxyphenyl)-1-phenylpropane, 1,1-bis(4-hydroxyphenyl)phenylethane, 2,2-bis(4-hydroxyphenyl)propane (bisphenol A (BPA)), 2,4-bis(4-hydroxyphenyl)-2-methylbutane, 1,3-bis[2-(4-hydroxyphenyl)-2-propyl]benzene (bisphenol M), 2,2-bis(3-methyl-4-hydroxyphenyl)propane, bis(3,5-dimethyl-4-hydroxyphenyl)methane, 2,2-bis(3,5-dimethyl-4-hydroxyphenyl)propane, bis(3,5-dimethyl-4-hydroxyphenyl)sulphone, 2,4-bis(3,5-dimethyl-4-hydroxyphenyl)-2-methylbutane, 1,3-bis[2-(3,5-dimethyl-4-hydroxyphenyl)-2-propyl]-benzene, 1,1-bis(4-hydroxyphenyl)cyclohexane and 1,1-bis(4-hydroxyphenyl)-3,3,5-trimethylcyclohexane (bisphenol TMC).

Particularly preferred bisphenols are 4,4'-dihydroxybiphenyl, 1,1-bis(4-hydroxyphenyl)phenylethane, 2,2-bis(4-hydroxyphenyl)propane (bisphenol A (BPA)), 2,2-bis(3,5-dimethyl-4-hydroxyphenyl)propane, 1,1-bis(4-hydroxyphenyl)cyclohexane and 1,1-bis(4-hydroxyphenyl)-3,3,5-trimethylcyclohexane (bisphenol TMC).

Suitable bisphenols are described, for example, in U.S. Pat. No. 2,999,835 A, U.S. Pat. No. 3,148,172 A, U.S. Pat. No. 2,991,273 A, U.S. Pat. No. 3,271,367 A, U.S. Pat. No. 4,982,014 A and U.S. Pat. No. 2,999,846 A, in the German published documents DE 15 70 703 A, DE 20 63 050 A, DE 20 36 052 A, DE 22 11 956 A and DE 38 32 396 A, the French patent text FR 1 561 518 A, in the monograph by H. Schnell, Chemistry and Physics of Polycarbonates, Interscience Publishers, New York 1964, p. 28ff; p. 102ff and by D. G. Legrand, J. T. Bendler, Handbook of Polycarbonate Science and Technology, Marcel Dekker New York 2000, p. 72ff.

In the case of the preparation according to the invention of homopolycarbonates, only one bisphenol is used, while in the case of the preparation according to the invention of copolycarbonates, a plurality of bisphenols are used; it goes without saying that the bisphenols used, like all other chemicals and auxiliaries added in the synthesis, can be contaminated with the impurities originating from their own synthesis, handling and storage, although it is desirable to employ very clean raw materials.

It may be emphasized here that the process of the invention can be used for virtually all known bisphenols.

The polycarbonates can be modified deliberately and in a controlled manner by use of small amounts of chain terminators and branching agents. Suitable chain terminators and branching agents are known from the literature. Some are described, for example, in DE-A 38 33 953. Preferred chain terminators are phenol or alkylphenols, in particular phenol, p-tert-butylphenol, isooctylphenol, cumylphenol, their chlorocarbonic esters or acid chlorides of monocarboxylic acids or mixtures of these chain terminators. Preferred chain terminators are phenol, cumylphenol, isooctylphenol and para-tert-butylphenol.

Examples of compounds suitable as branching agents are aromatic or aliphatic compounds having more than three, preferably three or four, hydroxy groups. Particularly suitable examples having three or more than three phenolic hydroxyl groups are phloroglucinol, 4,6-dimethyl-2,4,6-tri(4-hydroxyphenyl)-2-heptene, 4,6-dimethyl-2,4,6-tri(4-hydroxyphenyl)heptane, 1,3,5-tri(4-hydroxyphenyl)benzene, 1,1,1-tri(4-hydroxyphenyl)ethane, tri(4-hydroxyphenyl)phenylmethane, 2,2-bis[4,4-bis(4-hydroxyphenyl)cyclohexyl]-propane, 2,4-bis(4-hydroxyphenylisopropyl)phenol, tetra(4-hydroxyphenyl)methane.

Examples of other trifunctional compounds which are suitable as branching agents are 2,4-dihydroxybenzoic acid, trimesic acid, cyanuric chloride and 3,3-bis(3-methyl-4-hydroxyphenyl)-2-oxo-2,3-dihydroindole.

Particularly preferred branching agents are 3,3-bis(3-methyl-4-hydroxyphenyl)-2-oxo-2,3-dihydroindole and 1,1,1-tri(4-hydroxyphenyl)ethane.

The from 0.05 to 2 mol %, based on bisphenols used, of branching agents which may be concomitantly used can be introduced together with the bisphenols.

It should be ensured that the reaction components for the first step, viz. the transesterification, i.e. the bisphenols and the diaryl carbonates, are free of alkali metal ions and alkaline earth metal ions, although amounts of less than 0.1 ppm of alkali metal ions and alkaline earth metal ions can be tolerated. Bisphenols and diaryl carbonates having such a purity can be obtained by recrystallizing, washing or distilling the bisphenols and diaryl carbonates. In the process of the invention, the content of alkali metal ions and alkaline earth metal ions both in the bisphenol and in the diaryl carbonate should be <0.1 ppm.

The transesterification of the bisphenol and the diaryl carbonate in the melt is preferably carried out in two stages. In the first stage, the bisphenol and the diaryl carbonate are melted at temperatures of 80-250° C., preferably 100-230° C., particularly preferably 120-190° C., under atmospheric pressure over a period of 0-5 hours, preferably 0.25-3 hours. After addition of the catalyst, vacuum (down to 2 mm of Hg) is applied and the temperature is increased (to up to 260° C.) and the oligocarbonate is prepared from the bisphenol and the diaryl carbonate by distilling off the monophenol. The oligocarbonate prepared in this way has a weight average molecular weight $M_w$ (determined by measuring the relative solution viscosity in dichloromethane or in mixtures of equal weights of phenol/o-dichlorobenzene, calibrated by light scattering) in the range from 2000 to 18 000, preferably from 4000 to 15 000. Here, the major part of the monophenol (80%) is recovered from the process.

In the second stage of the polycondensation, the polycarbonate is prepared by further increasing the temperature to 250-320° C., preferably 270-295° C., at a pressure of <2 mm of Hg. The remainder of the monophenols is recovered here. Losses of monophenols of <5%, preferably <2%, particularly preferably <1%, can occur here due to the end groups in the polycarbonate and residual monophenol in the polycarbonate. These losses have to be compensated by appropriate amounts of monophenol for the preparation of the diaryl carbonate.

For the purposes of the process of the invention, catalysts for the transesterification of the bisphenol and the diaryl carbonate to form the polycarbonate are all inorganic or organic basic compounds, for example lithium, sodium, potassium, caesium, calcium, barium, magnesium hydroxides, carbonates, halides, phenoxides, diphenoxides, fluorides, acetates, phosphates, hydrogenphosphates, boranates, nitrogen and phosphorus bases such as tetramethylammonium hydroxide, tetramethylammonium acetate, tetramethylammonium fluoride, tetramethylammonium tetraphenylboranate, tetraphenylphosphonium fluoride, tetraphenylphosphonium tetraphenylboranate, dimethyldiphenylammonium hydroxide, tetraethylammonium hydroxide, DBU, DBN or guanidine systems such as 1,5,7-triazabicyclo[4.4.0]dec-5-ene, 7-phenyl-1,5,7-triazabicyclo[4.4.0]dec-5-ene, 7-methyl-1,5,7-triazabicyclo[4.4.0]dec-5-ene, 7,7'-hexylidenedi-1,5,7-triazabicyclo[4.4.0]dec-5-ene, 7,7'-decylidenedi-1,5,7-triazabicyclo[4.4.0]dec-5-ene, 7,7'-dodecylidenedi-1,5,7-triazabicyclo[4.4.0]dec-5-ene or phosphazenes such as the phosphazene base $P_1$-t-Oct=tertoctyliminotris(dimethylamino)phosphorane, the phosphazene base $P_1$-t-Butyl=tertbutyliminotris(dimethylamino)phosphorane, BEMP=2-tert-butylimino-2-diethylamino-1,3-dimethylperhydro-1,3,2-diaza-2-phosphorane.

These catalysts are used in amounts of from $10^{-2}$ to $10^{-8}$ mol, based on 1 mol of bisphenol.

The catalysts can also be used in combination with one another (two or more thereof).

When alkali metal/alkaline earth metal catalysts are used, it can be advantageous to add the alkali metal/alkaline earth metal catalysts at a later point in time (e.g. after the oligocarbonate synthesis in the polycondensation in the second stage). The alkali metal/alkaline earth metal catalyst can be added, for example, as solid or as a solution in water, phenol, oligocarbonate or polycarbonate.

The concomitant use of alkali metal or alkaline earth metal catalysts does not contradict the abovementioned purity requirement for the reactants.

The reaction of the bisphenol and the diaryl carbonate to form the polycarbonate in the process of the invention can be carried out batchwise or preferably continuously, for example in stirred vessels, thin film evaporators, falling film evaporators, cascades of stirred vessels, extruders, kneaders, simple disc reactors and high-viscosity disc reactors.

The aromatic polycarbonates of the process of the invention should have weight average molecular weights $M_w$ of from 18 000 to 80 000, preferably from 19 000 to 50 000, determined by measuring the relative solution viscosity in dichloromethane or in mixtures of the same weights of phenol/o-dichlorobenzene, calibrated by light scattering.

It is advantageous to purify the monophenols eliminated in and isolated from the transesterification of the bisphenol and the diaryl carbonate to form the polycarbonate before they are used in the diaryl carbonate synthesis. The crude monophenols isolated in the transesterification process can, depending on transesterification conditions and distillation conditions, be contaminated with, inter alia, diaryl carbonates, the bisphenol, salicylic acid, isopropenylphenol, phenyl phenoxybenzoate, xanthone, the hydroxymonoaryl carbonate. The purification can be effected by the customary purification processes, i.e., for example, distillation or recrystallization. The purity of the monophenols is then >99%, preferably >99.8%, particularly preferably >99.95%.

The advantages of the integrated process of the invention for preparing diaryl carbonates and polycarbonates with thermal oxidation of the hydrogen chloride obtained in the preparation of diaryl carbonate by means of an oxygen-containing gas by the Deacon process to recover chlorine for the synthesis of phosgene are the more economical operation with avoidance of the production of hydrogen compared to a classical electrolysis.

The preparation of diaryl carbonates and polycarbonates in combination with the thermal oxidation of hydrogen chloride additionally offers, as a result of the production of a concentrated hydrochloric acid containing about 30% of hydrogen chloride, the opportunity of taking concentrated hydrochloric acid from the circuit for other uses if required. One possible use of this concentrated hydrochloric acid is in the food sector. For this purpose, the concentrated hydrochloric acid produced by the process of the invention can, for example, be brought to a sufficiently high purity for the food industry by, for example, absorptive after-purification over an activated carbon bed as is known from the prior art.

The process of the invention for preparing diaryl carbonates and polycarbonates can, if appropriate, be combined with other possible uses of the hydrogen chloride obtained in the preparation of diaryl carbonate, e.g. use as starting material for the preparation of ethylene dichloride in PVC production.

The process gas which still contains hydrogen chloride after the thermal oxidation of hydrogen chloride in the presence of a catalyst by the Deacon process is fed to a hydrogen chloride absorption plant; here, it is possible to feed in not only purified hydrogen chloride from a number of sources but also, depending on the subsequent oxidation process, an anolyte acid depleted in hydrochloric acid from a hydrogen chloride electrolysis or a sodium chloride solution depleted in sodium chloride from a chloralkali electrolysis.

Figure 3:
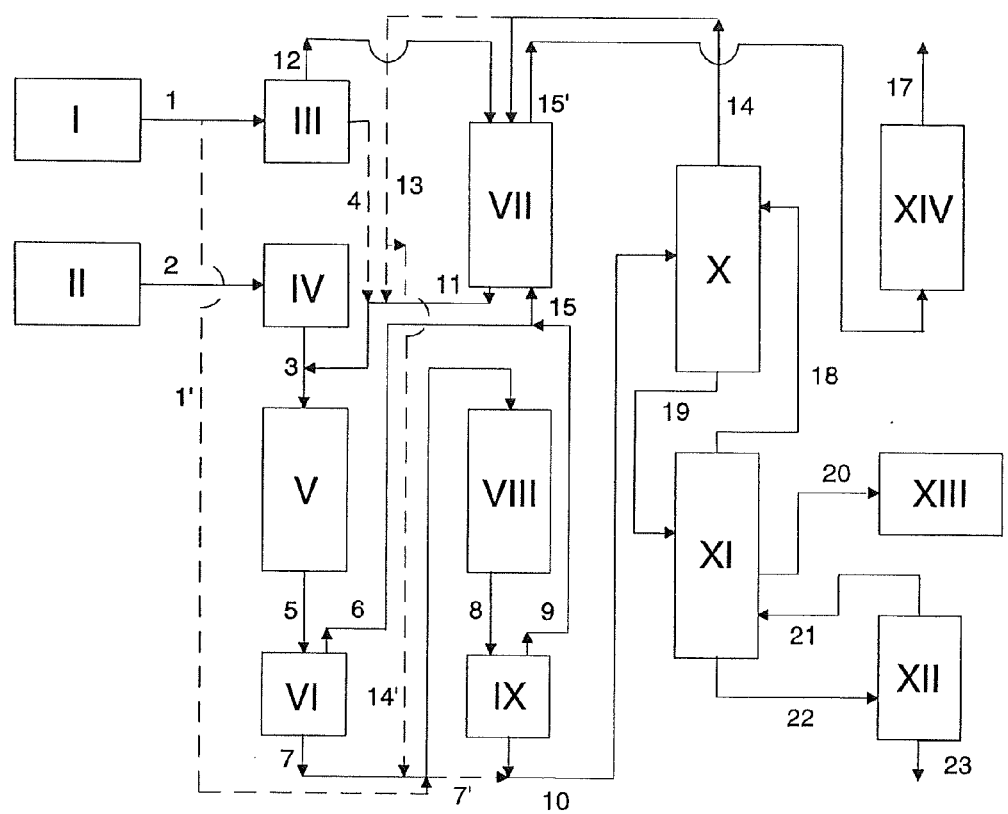
FIG. 3 illustrates a flow diagram of a process for the preparation of diphenyl carbonate by direct phosgenation of phenol in the presence of heterogeneous catalysts.

The following reference numerals have been used in FIG. 3:

I storage tank for phenol
II storage tank for phosgene
III, IV heat exchanger
V, VIII reactor
VI; IX degasser
VII countercurrent apparatus
X, XI, XII distillation column
XIII product vessel
XIV purification plant All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Figure 2:
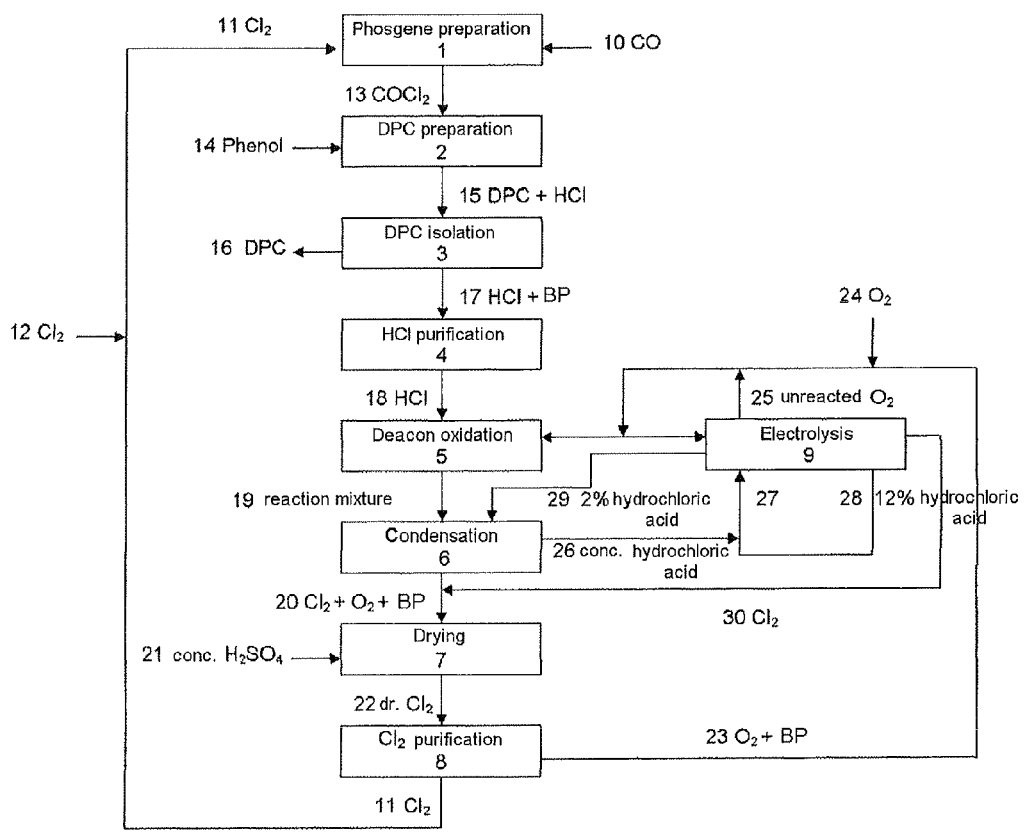
FIG. 2 illustrates a flow diagram of an integrated process for the preparation of diaryl carbonate (diphenyl carbonate, DPC) and recycling of the hydrogen chloride obtained.

The examples illustrate the process of the invention by means of the thermal oxidation of the hydrogen chloride obtained in the preparation of diphenyl carbonate to chlorine, the conversion of the chlorine into phosgene which can be used again in the process for preparing diphenyl carbonate (DPC process) (FIG. 2) with recirculation of the phenol formed in the preparation of polycarbonate to the preparation of diphenyl carbonate (FIG. 1).

In a first stage 1 of the preparation of diaryl carbonate (FIG. 2), chlorine 11 is reacted with carbon monoxide 10 to form phosgene 13. In the subsequent stage 2, phosgene 13 from stage 1 is reacted with a monophenol 14 (e.g. phenol) to form a mixture 15 of diaryl carbonate (e.g. diphenyl carbonate, DPC) and hydrogen chloride which is separated in stage 3 into diaryl carbonate 16, which is utilized, and HCl gas 17, which is subjected to a purification 4. The purified HCl gas 18 is reacted with oxygen in the HCl oxidation process 5, here in a Deacon process by means of catalyst.

The reaction mixture 19 from stage 5 is cooled (stage 6). Unreacted hydrogen chloride 26 which is obtained, possibly together with water or dilute hydrochloric acid, is discharged and fed to an electrolysis 9.

The gas mixture 20 obtained in this way, which consists of at least chlorine, oxygen and secondary constituents such as nitrogen, carbon dioxide, etc., is dried by means of concentrated sulphuric acid 21 (96% strength) (stage 7).

In a purification stage 8, chlorine 11 is separated from the gas mixture 22 from stage 7. The residual stream 23 comprising oxygen and secondary constituents is used in stage 5 (Deacon oxidation) and stage 9 (electrolysis). The electrolysis stage is an ODC electrolysis in which a gas diffusion electrode is used on the cathode side and oxygen is used as reactant.

The chlorine gas 11 obtained from the purification stage 8 can be directly reused in the phosgene synthesis 1.

The concentration of the hydrochloric acid 27 fed to the electrolysis cell 9 is from 14 to 15% by weight of HCl, and that of the hydrochloric acid 28 flowing out from the electrolysis cell 9 is from 11 to 13% by weight of HCl. The hydrochloric acid stream 28 is admixed with concentrated hydrochloric acid 26 from the separation stage 6 and fed back into the electrolysis cell 9.

The oxygen consumed in stages 5 and 9 is replaced by oxygen from an external source 24. The oxygen 25 which is not consumed in the cathode space of the electrolysis cell is circulated and admixed with fresh oxygen from an external source 24.

The about 2% strength by weight hydrochloric acid stream 29 which is likewise obtained in the cathode space is fed to the hydrochloric acid isolation 6 and there serves as absorption medium for excess gaseous hydrogen chloride.

The chlorine 30 prepared in stage 9 is combined with the chlorine-containing gas stream 20 and the combined gas stream is cooled in a single-stage or multistage cooling by means of a cooling apparatus, e.g. a shell-and-tube heat exchanger, and dried.

Drying 7 can, for example, be effected by means of a suitable desiccant in an absorption column provided with mass transfer elements. A suitable desiccant can be, as described for example in DE 10 235 476 A, either molecular sieves or hygroscopic adsorbents, e.g. sulphuric acid. Drying can be carried out in one or more stages. Drying is preferably carried out in two stages, with the chlorine to be dried being brought into contact with a sulphuric acid having a relatively low concentration, preferably from 70 to 80%, particularly preferably from 75 to 80%, in a first stage. In a second stage, the residual moisture is removed from the chlorine by means of a sulphuric acid having a higher concentration of preferably from 88 to 96%, particularly preferably 92-96%. The chlorine 22 which has been dried in this way and has a residual moisture content of preferably not more than 100 ppm, particularly preferably not more than 20 ppm, can be passed through a droplet precipitator to remove any sulphuric acid droplets still present therein.

The dried chlorine gas stream 22 is subsequently subjected to a chlorine purification 8.

The very pure chlorine 11 is supplemented by chlorine from an external source 12 and fed back into the preparation of phosgene 1.

Examples 1a-h

Preparation of Diphenyl Carbonate by Direct Phosgenation of Phenol

1a) Diphenyl Carbonate by Phosgenation of Phenol in the Presence of $\gamma$-$Al_2O_3$ The apparatus used for carrying out the process of the invention and the streams involved are shown schematically in FIG. 3.

41.12 parts by weight/h of phenol 1, fresh and/or recovered from the preparation of polycarbonate as described in Example 3) are taken from a heated vessel I and fed via heat exchanger III (60° C.) under atmospheric pressure from the top into a packed countercurrent column VII which is heated to 60° C. and in which mixing with phenol 14 taken from the top of the distillation column X takes place. After the offgas stream 15 originating from the degassing apparatus VI and IX has flowed through VII, mixture 11 (weight ratio of phenol/phosgene about 97/3) is fed in at the bottom. From storage tank II 21.93 parts by weight/h of phosgene 3 preheated by means of heat exchanger IV (170° C.) are introduced together with 11 in countercurrent into a reactor V which is filled with 150 parts by volume of $\gamma$-aluminium oxide and is heated to 170° C.

The product 5 exiting at the bottom of the reactor, which contains phenol, phenyl chloroformate, diphenyl carbonate and by-products in a ratio of 56.1/0.8/42.8/0.3 is separated by means of the degasser VI into offgas 6 (weight ratio of phenol, phosgene, hydrogen chloride and carbon dioxide=2.5/15.8/81.1/0.6) and bottoms 7 (weight ratio of phenol, phenyl chloroformate, diphenyl carbonate and by-products=55.8/0.9/43.0/0.3).

The phenyl chloroformate present in the bottoms 7 is converted into diphenyl carbonate by after-reaction with phenol present (possibly after addition of additional phenol (1' or 14')) at 180° C. in an after-reactor VIII, likewise filled with $\gamma$-aluminium oxide (150 parts by volume).

The product 8 (weight ratio of phenol, diphenyl carbonate and by-products=55.4/44.3/0.3) taken off at the bottom of the reactor is separated by means of degasser IX into offgas 9 (phenol/hydrogen chloride) and bottoms 10 (weight ratio of phenol, diphenyl carbonate and by-products=55.2/44.5/0.3).

Bottoms 10 are fed into a first distillation column X and separated at about 80° C./16 mbar (12 mm) into 57.7 parts by weight/h of phenol and bottoms 19 (weight ratio of phenol, diphenyl carbonate and by-products=0.3/99.1/0.6). Bottoms 19 are introduced into a second distillation column XI in which phenol still present (0.14 part by weight) is removed at the top and is returned to the upper part of the first column X. The product 22 (weight ratio of diphenyl carbonate/by-products=88.6/11.4) taken off at the bottom is separated in a third distillation column XII at 170° C./12 mm into overhead product 21 (2.3 parts by weight/h of diphenyl carbonate), which is recirculated to the lower part of the second column XI, and bottoms 23 (high-boiling by-products). Discharge at the side from the gas space of the 2nd column XI gives 46.6 parts by weight/h of product 20 (weight ratio of diphenyl carbonate, phenol=99.8/0.2) filled in product container XIII.

Offgas streams 6 and 9 are combined to form 15 (weight ratio of phenol, hydrogen chloride and carbon dioxide=5.8/93.6/0.6) and passed through phenol in the countercurrent apparatus VII. The offgas 15' exiting at the top is subjected to a purification plant XIV, in which hydrogen chloride is freed from phenol by freezing out.

1b) Phosgenation of Phenol in the Presence of $TiCl_4$ in a Reactive Distillation Column 49.9 parts by weight/h of molten phenol and 0.25 part by weight/h of $TiCl_4$ are metered from the top under atmospheric pressure into a reactive distillation column thermostated to 160° C. and having 10 plates each occupying 18 parts by volume and at the same time 25.1 parts by weight/h of phosgene heated to the same temperature are introduced in countercurrent at the bottom.

The product exiting at the bottom, which contains phenyl chloroformate and diphenyl carbonate in a weight ratio of 3:97 (phenol conversion 69.5%, selectivity 99.6%), is, after reaction of the phenyl chloroformate present with phenol to form diphenyl carbonate in a residence reactor, isolated and separated by degassing into offgas and bottoms.

The offgas stream exiting at the top of the reactive distillation plant is combined with the offgas from the degassing and freed from small amounts of phosgene and phenol by freezing-out.

The phosgene conversion was measured by determining the phosgene content in a gas mouse installed in the offgas stream by reaction with excess ethanol and correlation of the ethyl chloroformate and diethyl carbonate formed with the amount of unreacted phosgene.

1c) Phosgenation of Phenol in the Presence of $TiCl_4$ in a Reactive Distillation Column 187.3 parts by weight/h of molten phenol and 0.42 part by weight/h of $TiCl_4$ are metered from the top under atmospheric pressure into a reactive distillation apparatus thermostated to 150° C. and having 20 plates each occupying 43 parts by volume and at the same time 62.7 parts by weight/h of phosgene heated to the same temperature are introduced in countercurrent at the bottom.

The product exiting at the bottom, which contains phenol, phenyl chloroformate, diphenyl carbonate and by-products (weight ratio=31.7/5.2/62.8/0.3) (phosgene conversion 83.5%, phenol conversion 64.8%, selectivity 99.7%), is, after reaction of the phenyl chloroformate present with phenol to form diphenyl carbonate in a residence reactor, isolated and separated by degassing into offgas and bottoms (weight ratio of phenol, diphenyl carbonate and by-products=29.2/70.4/0.4).

Distillation gives 99.8% pure diphenyl carbonate.

The offgas stream exiting at the top of the reactive distillation plant is combined with the offgas from the degassing and freed from small amounts of phosgene and phenol by freezing-out.

1d) Phosgenation of Phenol in the Presence of $AlCl_3$ in a Reactive Distillation Column 399.0 parts by weight/h of molten phenol and 0.61 part by weight/h of $AlCl_3$ are metered from the top under atmospheric pressure into a reactive distillation apparatus thermostated to 150° C. and having 20 plates each occupying 43 parts by volume and at the same time 100.0 parts by weight/h of phosgene heated to the same temperature are introduced in countercurrent at the bottom.

The product exiting at the bottom, which contains phenol, phenyl chloroformate, diphenyl carbonate and by-products (weight ratio=60.7/3.5/34.8/0.6) (phosgene conversion 71.6%, phenol conversion 35.4%, selectivity 99%), is, after reaction of the phenyl chloroformate present with phenol to form diphenyl carbonate in a residence reactor, isolated and separated by degassing into offgas and bottoms (weight ratio of phenol, diphenyl carbonate and by-products=59.6/39.6/0.8).

The offgas is combined with the offgas stream leaving the top of the reactive distillation plant and freed from small amounts of phosgene and phenol by freezing-out.

Distillation at 172° C./22 mbar gives 99.7% pure diphenyl carbonate

1e) Phosgenation of Phenol in the Presence of $ZrCl_4$ in a Bubble Column Cascade 24.8 parts by weight/h of phosgene heated to the same temperature are introduced from the bottom over 3 hours under atmospheric pressure through a gas frit into two bubble columns which are connected in series and thermostated to 160° C. and each have a volume of 100 parts by volume charged with 141.0 parts by weight of molten phenol and 0.88 part by weight/h of $ZrCl_4$.

The reaction mixture from the 1st bubble column, which contains phenyl chloroformate and diphenyl carbonate in a weight ratio of 2:98 (phenol conversion 83.4%, selectivity 98.3%) is, after reaction of the phenyl chloroformate present with phenol to form diphenyl carbonate in a residence reactor, isolated and separated by degassing into offgas and bottoms which are separated by distillation.

The offgas stream exiting at the top of the first bubble column is introduced through a gas frit into the 2nd bubble column. The phenol conversion in the 2nd bubble column is 22.0% after 3 h.

1f) Phosgenation of Phenol in the Presence of $TiCl_4$ in a Bubble Column Cascade After carrying out the direct phosgenation as described in 1e) but using 0.71 part by weight of $TiCl_4$, the reaction mixture in the 1st bubble column contains phenyl chloroformate and diphenyl carbonate in a weight ratio of 0.6:99.4 (phenol conversion 80.2%, selectivity 99.5%). The phenol conversion in the 2nd bubble column is 12.3%.

1g) Phosgenation of Phenol in the Presence of $Ti(OC_6H_5)_4$ in a Bubble Column Cascade After carrying out the direct phosgenation as described in 1e) but using 1.57 parts by weight of $Ti(OC_6H_5)_4$, the reaction mixture in the 1st bubble column contains phenyl chloroformate and diphenyl carbonate in a weight ratio of 0.7:99.3 (phenol conversion 81.5%, selectivity 99.4%). The phenol conversion in the 2nd bubble column is 17.4%.

1h) Phosgenation of Phenol in the Presence of $TiCl_4$ in the Gas Phase 25.0 parts by weight/h of molten phenol, 0.61 part by weight/h of $TiCl_4$ and 12.5 parts by weight/h of phosgene heated to the same temperature are metered from the top at atmospheric pressure into a tube reactor apparatus which is thermostated to 235° C. and packed with glass wool.

The product exiting at the bottom, which contains phenyl chloroformate and diphenyl carbonate in a weight ratio of 0.6:99.4 (phosgene conversion 87%, phenol conversion 59.8%, selectivity 99.9%), is, after reaction of the phenyl chloroformate present with phenol to form diphenyl carbonate in a residence reactor, isolated and separated by degassing into offgas and bottoms.

The hydrogen chloride obtained in the continuous preparation of diaryl carbonates by reaction of monophenols and phosgene in the presence of catalysts can, after removal of the small amount of phosgene and monophenol impurities, e.g. by freezing-out, be fed without complicated purification, optionally after treatment with activated carbon, to an electrochemical oxidation.

Examples 2a-b

Recycling of Hydrogen Chloride from the Preparation of Diphenyl Carbonate by Thermal Oxidation by Means of Oxygen and Electrolysis 2a) Recycling of Hydrogen Chloride from the Preparation of Diphenyl Carbonate by Thermal Oxidation by Means of Oxygen in Combination with an Electrolysis Using an Oxygen-Consuming Cathode A stream of 35.9 parts by weight/h of purified hydrogen chloride from a preparation of diaryl carbonate is divided into two substreams. 29.5 parts by weight/h are fed to an HCl oxidation and 6.4 parts by weight/h are fed to an HCl absorption. 29.5 parts by weight/h of HCl are fed together with 12.9 parts by weight/h of oxygen (content greater than 99%) to a catalytic HCl oxidation. The oxidation is carried out at 333° C. and 3.4 bar. The HCl conversion in the reactor is 85%. The gas mixture leaving the reactor is cooled to 100° C. and the HCl is condensed together with the water of reaction in an HCl absorption. For this purpose, a substream of the anolyte acid stream 28 which is depleted in hydrochloric acid coming from the electrolysis is passed into the hydrochloric acid 26 from the HCl absorption. 32.1 parts by weight/h of the anolyte acid 28 depleted in hydrochloric acid and having an HCl concentration of 12.2% by weight are fed to the HCl absorption. The cooled process gas stream (weight ratio of HCl, oxygen, chlorine and water=4.4/7.4/24.4/6.18) is passed together with 6.4 parts by weight/h of purified hydrogen chloride into the HCl absorption. This HCl absorption unit produces a 30% strength by weight hydrochloric acid 26 which is combined with the remainder of the depleted anolyte acid 28 and fed back into the electrolysis cell. 2.96 parts by weight/h of the depleted anolyte acid 28 are discharged from the anolyte acid circuit.

The electrolysis is carried out at a current density of 5 kA/m$^2$ at 55° C. and a potential of 1.39 V. A palladium-stabilized titanium is used as anode and cathode material. 10.1 parts by weight/h of chlorine are evolved at the ruthenium oxide-coated anode from DENORA, Germany. Anode half shell and cathode half shell are separated by an ion-exchange membrane Nafion 324 from DUPONT. As cathode, use is made of an oxygen-consuming cathode from ETEK, which contains a rhodium sulphide-supported catalyst. Oxygen is fed in an excess of 100%, i.e. in an amount of 9.17 parts by weight/h, to the cathode half element. The oxygen is recycled to the electrolysis; a purge stream of 1% of the feed amount is discharged (not shown) downstream of the electrolysis 9 or is used in the HCl oxidation 5. The pressure in the anode half cell is higher than that in the cathode half cell. The differential pressure is 200 mbar. A condensate stream of 8.8 parts by weight/h is taken from the cathode half cell.

The electrolysis unit 9 comprises 615 electrolysis segments, with each element comprising an anode half shell with anode, an ion-exchange membrane and a cathode half shell with oxygen-consuming cathode.

2b) Recycling of Hydrogen Chloride from the Preparation of Diphenyl Carbonate by Thermal Oxidation by Means of Oxygen in Combination with a Chloralkali Electrolysis The oxidation is carried out as described in 2a).

As in Example 1, a purified HCl gas stream of 35.9 parts by weight/h from a preparation of diaryl carbonate is fed to the thermal HCl oxidation together with a 100% excess of oxygen, i.e. 15.7 parts by weight/h of oxygen. The conversion is 85%, so that 5.4 parts by weight/h of HCl, 9.0 parts by weight/h of oxygen, 7.5 parts by weight/h of water and 29.7 parts by weight/h of chlorine leave the reactor. This process gas 19 is fed to an HCl absorption which is operated using a first substream of 177.8 parts by weight/h of an NaCl-depleted NaCl-containing solution (18.3% by weight of NaCl) from an NaCl electrolysis. The water and the hydrogen chloride of the process gas 19 are absorbed in this NaCl-containing solution. The stream leaving the absorption has the following composition: 152.8 parts by weight/h of water, 32.5 parts by weight/h of NaCl, 5.4 parts by weight/h of hydrogen chloride. This stream is subsequently combined with the second substream of the NaCl-containing solution of 118.2 parts by weight/h, admixed with 26.4 parts by weight/h of solid NaCl and fed back into the NaCl electrolysis. The NaCl electrolysis comprises 1475 bipolar electrolysis elements each having a membrane area of 2.71 m$^2$. The NaCl electrolysis is operated using anode half shells made of titanium which bear a titanium anode coated with noble metal oxide. The cathode half shell comprises nickel and bears a nickel cathode coated with noble metal oxide. Anode half shell and cathode half shell are separated by an ion-exchange membrane Nafion 982 from DUPONT. 21.2 parts by weight/h of chlorine are produced at the anode and 74.8 parts by weight/h of sodium hydroxide solution having a concentration of 32% by weight and 0.6 part by weight/h of hydrogen are produced at the cathode. The NaCl-depleted anolyte is partly fed back to the HCl absorption.

Example 3

Preparation of Polycarbonate

From a reservoir, 8600 parts by weight/h of melt mixture comprising 4425 parts by weight/h of diphenyl carbonate, prepared as described in 1a) or 1b), and 4175 parts by weight/h of bisphenol A, with addition of 0.52 part by weight/h of the phenol adduct of tetraphenylphosphonium phenoxide containing 65.5% of tetraphenylphosphonium phenoxide/h dissolved in 4.5 parts by weight/h of phenol/h, are pumped through a heat exchanger, heated to 190° C. and conveyed through a residence column at 12 bar and 190° C. The average residence time is 50 minutes.

The melt is then introduced via a depressurization valve into a separator which is under a pressure of 200 mbar. The melt flowing out is reheated to 189° C. in a falling film evaporator which is likewise under 200 mbar and collected in a receiver. After a residence time of 20 minutes, the melt is pumped into the next three, similarly constructed stages. The conditions in the 2nd/3rd/4 the stages are 100/74/40 mbar, 218/251/276° C. and 20/10/10 minutes. The oligomer formed has a relative viscosity of 1.09. All vapours are conveyed via pressure regulators into a column which is under vacuum and discharged as condensates.

The oligomer is then condensed further in an attached basket reactor at 278° C. and 3.0 mbar at a residence time of 45 minutes to give a higher molecular weight product. The relative viscosity is 1.195. The vapours are condensed.

A substream of 150 parts by weight/h of melt are branched off by means of a gear pump from the melt stream which is introduced into a further basket reactor, admixed with 0.185 part by weight/h of a 5% strength aqueous phosphoric acid, stirred by means of a static mixer having a length-to-diameter ratio of 20 and reintroduced into the main melt stream. Immediately after the streams combine, the phosphoric acid is homogeneously distributed in the total melt stream by means of a further static mixer.

The melt which has been treated in this way is further subjected to the process conditions in a further basket reactor at 284° C., 0.7 mbar and an average residence time of 130 minutes, discharged and pelletized.

The vapours are condensed in the vacuum plant and downstream thereof.

The polycarbonate obtained has the following properties: relative viscosity 1.201/phenolic OH 255 [ppm]/DPC 71 [ppm]/BPA 6 [ppm]/phenol 56 [ppm].

The phenol which has been distilled off can be recirculated to the preparation of diphenyl carbonate in step (b), as described in Examples 1a-h).

What is claimed:

1. A process for preparing diaryl carbonate, which comprises the steps of:
   (a) preparing phosgene by reaction of chlorine with carbon monoxide;
   (b) reacting the phosgene formed in step (a) with at least one monophenol in the presence of a homogeneous metal catalyst to form at least one diaryl carbonate and hydrogen chloride;
   (c) isolating and working-up the diaryl carbonate formed in step (b);
   (d) isolating and optionally purifying the hydrogen chloride formed in step (b);
   (e) thermally oxidizing at least part of the hydrogen chloride from step (d) to chlorine by oxygen forming a gas mixture with formation of water; and
   (f) recirculating at least part of the chlorine prepared in step (e) to the preparation of phosgene in step (a);
   wherein the thermal oxidation by oxygen in step (e) is carried out using one or more catalyst, and wherein the catalyst is selected from the group consisting of titanium chloride, zirconium chloride, aluminum chloride and titanium phenoxide.

2. The process according to claim 1, further comprising
   1) cooling the gas mixture formed in step (e) to condense aqueous hydrochloric acid;
   2) separating off the resulting aqueous solution of hydrogen chloride hydrochloric acid from the gas mixture;
   3) feeding at least part of the aqueous hydrochloric acid which has been separated off from the gas mixture to an electrochemical oxidation step in which at least part of the aqueous hydrochloric acid is oxidized to chlorine gas;
   4) optionally adding the chlorine gas obtained from the electrochemical oxidation in step 3) to the gas mixture obtained in step (e);
   5) removing residual amounts of water present in the gas mixture from steps 3) and (e) to give a chlorine-rich gas mixture;
   6) freeing the resulting chlorine-rich gas mixture from oxygen and optionally from secondary constituents.

3. The process according to claim 1, wherein the hydrogen chloride formed in step (b) is purified in step (d) by removing the phosgene by liquefaction.

4. The process according to claim 1, wherein the hydrogen chloride is purified in step (d) by freezing-out.

5. The process according to claim 2, wherein the separation of the aqueous hydrochloric acid from the gas mixture in steps 2) comprises scrubbing of the gas mixture with water or dilute hydrochloric acid.

6. The process according to claim 2, wherein the electrochemical oxidation of the aqueous hydrogen chloride solution in step 3) is carried out in an electrolysis cell in which an anode space and a cathode space are separated by an ion-exchange membrane.

7. The process according to claim 2, wherein the electrochemical oxidation of the aqueous hydrochloric acid in step 3) is carried out in an electrochemical cell in which an anode space and a cathode space are separated by a diaphragm.

8. The process according to claim 2, wherein the electrochemical oxidation of the aqueous hydrochloric acid in step 3) comprises a gas diffusion electrode as a cathode.

9. The process according to claim 8, wherein the gas diffusion electrode is operated as an oxygen-depolarized cathode.

10. The process according to claim 8, wherein the cathode comprises rhodium sulphide.

11. The process according to claim 2, wherein the hydrochloric acid is oxidized in step 3) together with alkali metal chlorides.

12. The process according to claim 2, wherein the hydrochloric acid is oxidized in step 3) together with sodium chloride, in an anodic chloralkali electrolysis.

13. The process according to claim 12, wherein a depleted alkali metal chloride solution from the chloralkali electrolysis is used as alkali metal chloride solution.

14. The process according to claim 2, wherein part of the hydrogen chloride provided for the thermal oxidation in step (e) is branched off, subjected to absorption in water or dilute hydrochloric acid to give a concentrated solution, which is combined with the aqueous hydrochloric acid from step 2) and fed to the electrochemical oxidation in step 3).

15. The process according to claim 1, wherein the chlorine is converted into phosgene as per step (a) and the resulting phosgene is used for the reaction with phenol to form diphenyl carbonate in step (b).

16. The process according to claim 1, wherein the thermal oxidation in step (e) is operated at a conversion of from 50 to 98%.

17. The process according to claim 2, wherein the gas mixture formed in the reaction in step (e) consists of chlorine and water, unreacted hydrogen chloride and oxygen, and carbon dioxide and nitrogen.

18. The process according to claim 2, wherein the thermal oxidation in step (e) is operated at a conversion of from 60 to 95%; and wherein the removal of the residual amounts of water in step 5) is carried out by scrubbing with sulphuric acid.

* * * * *